(12) United States Patent
Penenberg

(10) Patent No.: US 7,396,328 B2
(45) Date of Patent: Jul. 8, 2008

(54) SURGICAL RETRACTOR WITH ATTACHMENT

(75) Inventor: Brad L. Penenberg, Beverly Hills, CA (US)

(73) Assignee: Wright Medical Technology, Inc., Arlington, TN (US)

(*) Notice: Subject to any disclaimer, the term of this patent is extended or adjusted under 35 U.S.C. 154(b) by 186 days.

(21) Appl. No.: 11/354,537

(22) Filed: Feb. 15, 2006

(65) Prior Publication Data

US 2006/0189848 A1 Aug. 24, 2006

Related U.S. Application Data

(60) Provisional application No. 60/654,426, filed on Feb. 18, 2005.

(51) Int. Cl.
*A61B 1/32* (2006.01)
(52) U.S. Cl. ..................... 600/201; 600/210
(58) Field of Classification Search ........... 600/201, 600/205, 210, 217; 606/90, 96
See application file for complete search history.

(56) References Cited

U.S. PATENT DOCUMENTS

| | | | |
|---|---|---|---|
| 4,686,972 A * | 8/1987 | Kurland .................. 606/96 |
| 5,027,793 A * | 7/1991 | Engelhardt et al. ......... 600/210 |
| 5,303,694 A | 4/1994 | Mikhail |
| 5,342,366 A | 8/1994 | Whiteside |
| 5,895,352 A | 4/1999 | Kleiner |
| 5,928,139 A * | 7/1999 | Koros et al. .............. 600/205 |
| 6,056,689 A | 5/2000 | Lenox |
| 6,083,154 A * | 7/2000 | Liu et al. ................. 600/234 |
| 6,206,826 B1 | 3/2001 | Mathews |
| 7,108,698 B2 * | 9/2006 | Robbins et al. ............ 606/90 |
| 2003/0236447 A1* | 12/2003 | Ritland ................... 600/210 |
| 2006/0089536 A1* | 4/2006 | Perez-Cruet et al. ....... 600/210 |

OTHER PUBLICATIONS

Innomed Instrument Division Product Brochure (2000).

* cited by examiner

*Primary Examiner*—Cary E O'Connor

(57) ABSTRACT

A retractor configured for anchorage to the acetabular area of the hip bone via a bendable pin, such that the bent pin retains the retractor in a selected position. The retractor includes a site anchor portion, with a spacer portion extending upward from a leading end of the site anchor portion. At least one retainer track is affixed to the spacer portion, the track being configured to closely receive the bendable pin. The leading end of the site anchor portion is preferably angled and serrated. The site anchor portion preferably has a curved configuration for use in resting the leading end of the site anchor portion substantially along an outer portion of a rim of the acetabulum. The retractor may be provided with an extension portion. The extension portion is preferably angled and serrated.

19 Claims, 4 Drawing Sheets

SURGICAL RETRACTOR WITH ATTACHMENT

CROSS REFERENCE TO RELATED APPLICATIONS

This application claims priority to and incorporates by reference Provisional Patent Application Ser. No. 60/654,426, filed Feb. 18, 2005, which is pending.

FIELD OF THE INVENTION

The present invention relates to surgery, and is particularly adapted for use in minimally invasive orthopedic procedures.

BACKGROUND OF THE INVENTION

Exposure to a surgical operating site requires stretching of the surrounding soft tissues to allow for better visualization. Minimally invasive surgery ("MIS") typically presents challenges in the area of exposure and visualization, and sometimes requires more retractors than a typical incision surgery. In MIS surgeries, it is often necessary to use additional personnel, such as nurses, to manipulate the various retractors.

U.S. Pat. No. 5,303,694 (Mikhail) discloses the use of Steinmann pins for holding a retractor in a hip procedure. The retractor has a pair of hinged wing members that include a tubular pin guide for receiving a Steinman pin. The retractor also includes a bore along the pivot point for receiving a Steinman pin. However, the Mikhail patent does not teach or suggest bending or otherwise deforming the Steinmann pins in order to retain the retractor in position. See also U.S. Pat. No. 6,206,826 (Mathews et al.).

There is thus a need for a surgical retractor and a method of use having the following characteristics and advantages over the prior art.

OBJECTS AND SUMMARY OF THE INVENTION

It is an object of the invention to provide a retractor that readily anchors in a surgical site.

It is an object of the invention to provide a retractor that is particularly adapted for use in a minimally invasive orthopedic surgery.

The foregoing and other objects and advantages of the invention are achieved by providing a retractor instrument assembly for use in a hip procedure in an acetabular area of a hip bone of a patient through an incision in the skin of the patient, comprising, generally, a unibody retractor configured for anchorage to the hip bone via a bendable pin. The retractor includes a site anchor portion, with a leading end of the site anchor portion sized and configured to pass through a minimally invasive incision. A spacer portion of the site anchor portion extends upward from the leading end. The leading end of the site anchor portion is preferably angled. The leading end of the site anchor portion is preferably serrated. The site anchor portion preferably has a curved configuration for use in resting the leading end of the site anchor portion substantially along an outer portion of a rim of the acetabulum. The spacer portion has a narrow width to minimize tension in the skin along the incision. A surface support portion extends laterally from the spacer portion. A handle portion extends from the surface support portion, with the handle portion being configured for use in manipulating the retractor to retract the incision. At least one retainer track is affixed to the spacer portion. The retainer track is configured to closely receive a bendable pin therethrough for use in securing the retractor to the bone in a selected position. In the assembled form, at least one bendable pin passes through the retainer track of the retractor. A leading end of the bendable pin extends below the leading end of the site anchor portion. A bend is formed in the pin above a trailing end of the retainer track, such that the bend prevents the retractor from sliding toward the trailing end of the bendable pin.

The retainer track is preferably a hollow tubular body having a continuous sidewall. The retainer track is preferably positioned along a side of the spacer portion. The retractor is preferably provided with a pair of retainer tracks, with the retainer tracks positioned along opposing sides of the spacer portion. The retractor is preferably provided with an extension portion extending laterally along the leading end of the site anchor portion. The extension portion has a curved configuration for use in resting the extension portion substantially along an outer portion of a rim of the acetabulum. A leading end of the site anchor portion preferably angles downward toward the extension portion, and the extension portion in turn continues to angle downward, so as to form a generally continuous angled leading edge for use in placing the retainer in a desired position along the acetabular rim of the patient. The generally continuous angled leading edge is preferably serrated.

The retractor assembly can be provided in the form of a kit, with the kit including a retractor of the type described herein and at least one bendable pin. The pin is of sufficient rigidty to allow a leading end of the pin to be affixed to the hip bone while the pin is retained in the retainer track, yet sufficiently bendable to allow a bend to be formed in the pin above a trailing end of the retainer track without dislodging the leading end of the pin from the bone, such that the bend in the pin retains the retractor in a selected position by preventing the retractor from translating upward along the pin. Methods of using the instrument assembly kit form part of the invention, as described herein.

The foregoing and other objects, features, aspects and advantages of the invention will become more apparent from the following detailed description of the invention when considered in conjunction with the accompanying drawings.

PREFERRED EMBODIMENTS OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
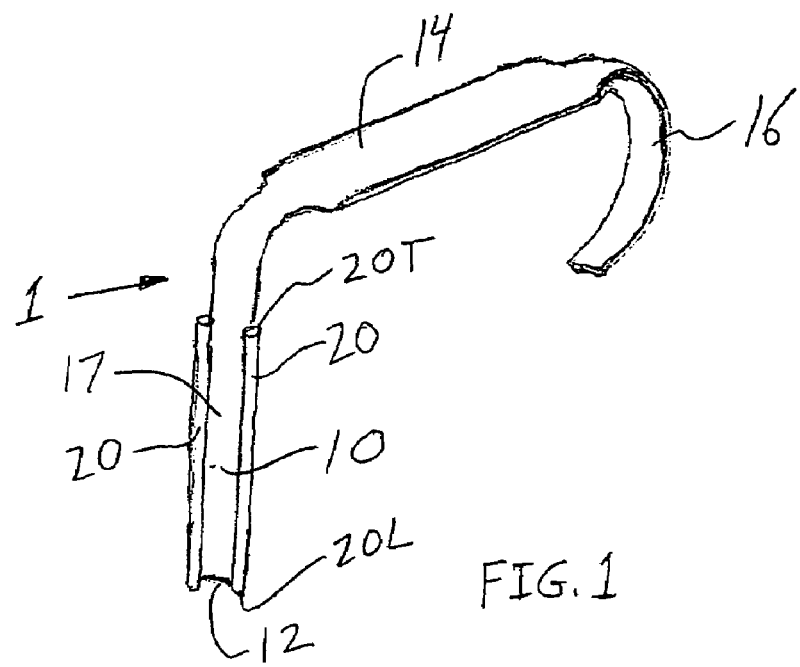
FIG. 1 is a front-side perspective view of one preferred embodiment of a retractor of the invention.
Figure 3:
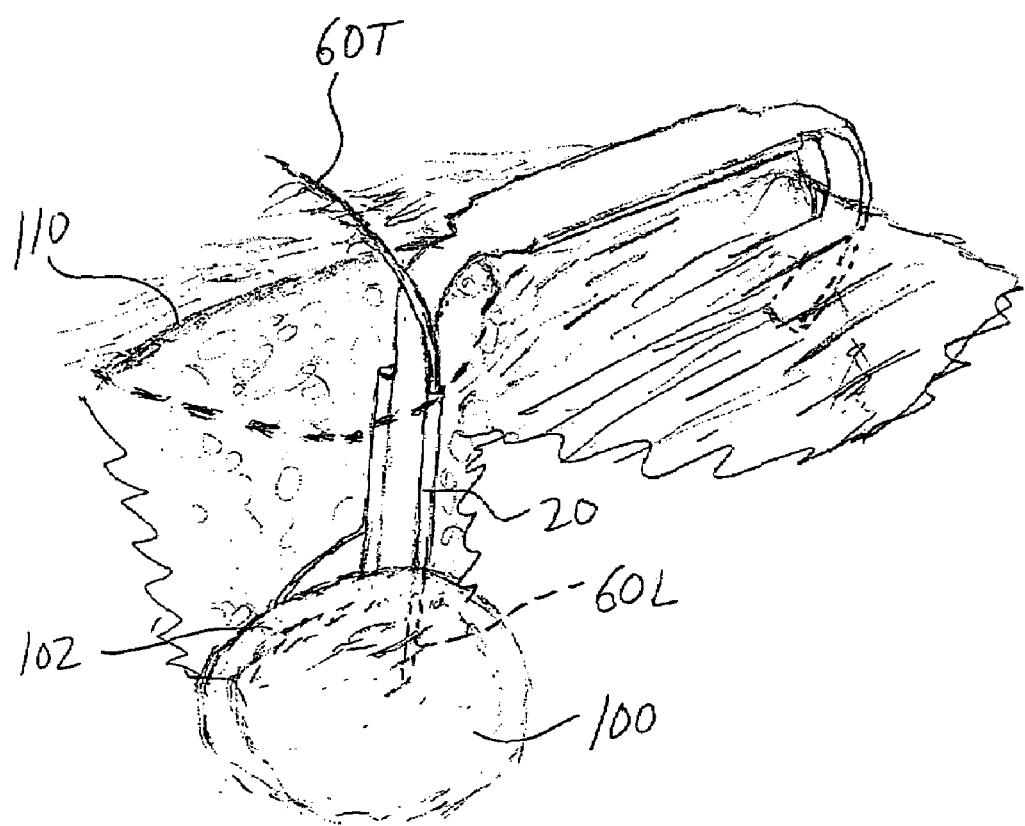
FIG. 3 is a perspective view showing the retractor of FIGS. 2A-2B in use in a minimally invasive hip procedure.
Figure 4:
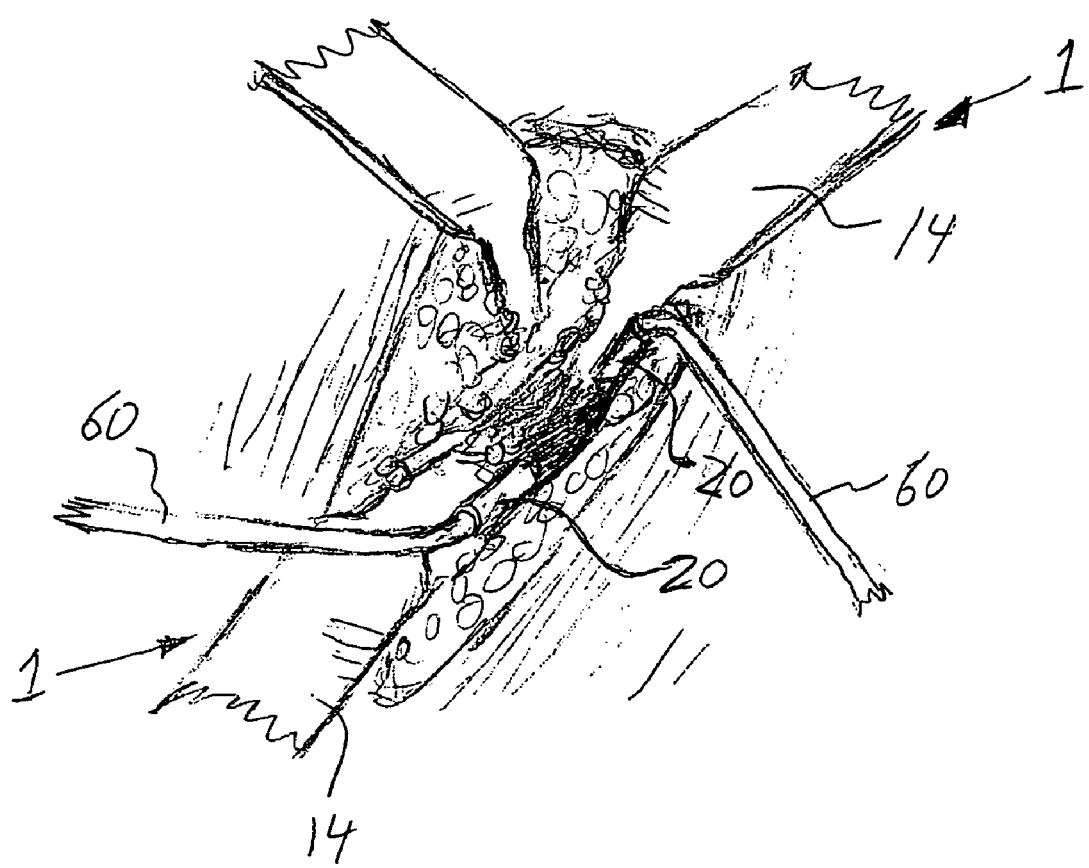
FIG. 4 is a top view showing retractors of the invention in use in a minimally invasive hip procedure.

As shown in FIG. 4, the invention is directed to securing a retractor 1 using a bent pin 60. The pin 60 is preferably a Steinmann pin having a diameter of ⅛ inch (3.2 mm). As shown in FIG. 1, a specially configured retractor 1 is used in the procedure. The retractors shown in FIGS. 1-4 are configured particularly for use in a minimally invasive hip procedure. The retractor 1 includes a site anchor portion 10, which is configured to pass through an incision and into a surgery site. The embodiment of FIG. 1 includes a narrow site anchor portion 10, which allows the site anchor portion 10 to pass through a minimally invasive incision. The site anchor portion 10 of the retractor 1 shown in FIG. 1 includes a spacer portion 17 having a lengthwise dimension that is sized to allow the site anchor portion to extend from the incision area to a selected bone or bone region 100 of the patient (see e.g. FIG. 3). As indicated in the drawings (particularly FIG. 3), the spacer portion 17 has a narrow width in order to minimize tension in the skin along the incision. The spacer portion 17 preferably has a width of between about 10 mm to about 40 mm, and most preferably of about 16 mm. A surface support portion 14 extends from the site anchor portion 10 in the manner of a conventional retractor. A handle portion 16 extends from the surface support portion in the manner of a conventional retractor, and is configured for use in manually manipulating retractor 1 to retract the incision 110.

As shown in FIG. 1, the site anchor portion 10 is provided with at least one retainer track 20, and is preferably provided with two retainer tracks 20. As indicated in FIGS. 3 and 4, the retainer track 20 is configured to receive a pin 60 for use in securing the retractor 1 in a selected position. In a preferred embodiment, the retainer track 20 is a hollow tubular body having a continuous sidewall, which can be welded to the site anchor portion 10. Other configurations could be used for the retainer track 20, such as a plurality of axially aligned rings or a tube having openings along the side, provided that the retainer track 20 prevents translation of the retractor 1 relative to the pin 60, except along the length of the pin 60. As indicated in FIGS. 3 and 4, translation of the retractor 1 along the pin 60 is selectively prevented by bending the pin 60 while a leading portion 60L of the pin 60 is engaged in bone, such that a portion of the pin 60 prevents the retractor 1 from translating upward along the pin 60, i.e. from sliding toward the trailing end of the pin 60. Unlike the pivoting retractor disclosed in U.S. Pat. No. 5,303,694 (Mikhail), the retractor 1 of the present invention features a rugged, uni-body configuration.

Figure 2A:
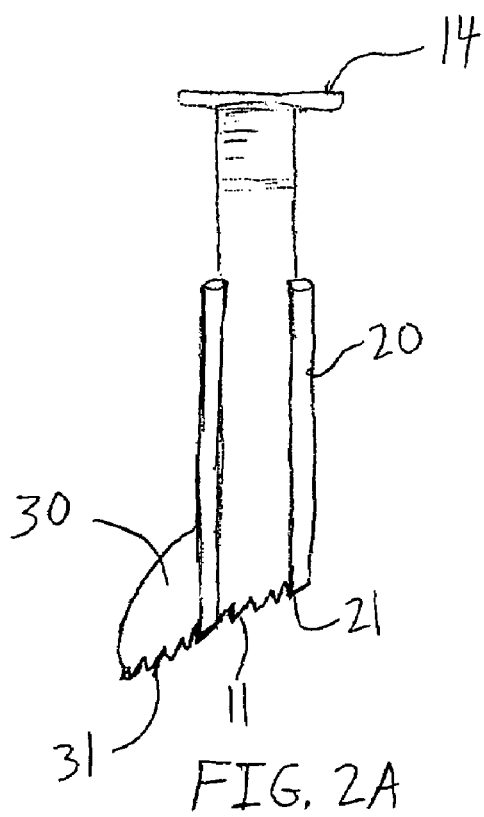
FIG. 2A is a front view of one preferred embodiment of a retractor of the invention.
Figure 2B:
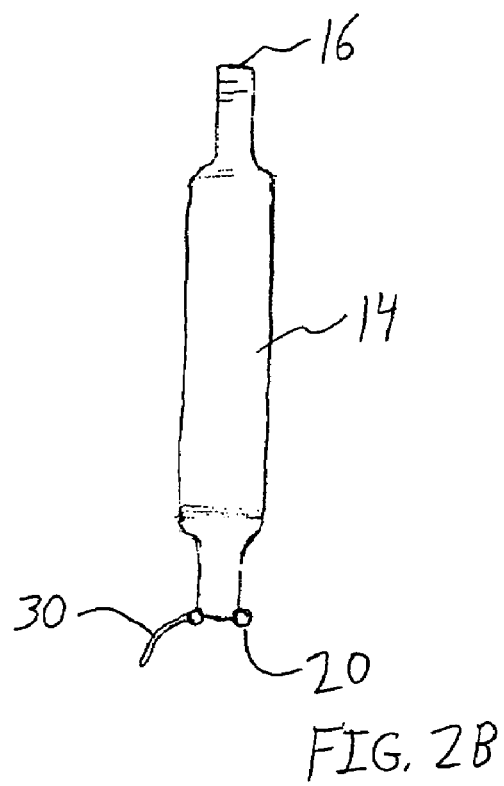
FIG. 2B is a top view of one preferred embodiment of a retractor of the invention.
Figure 2C:
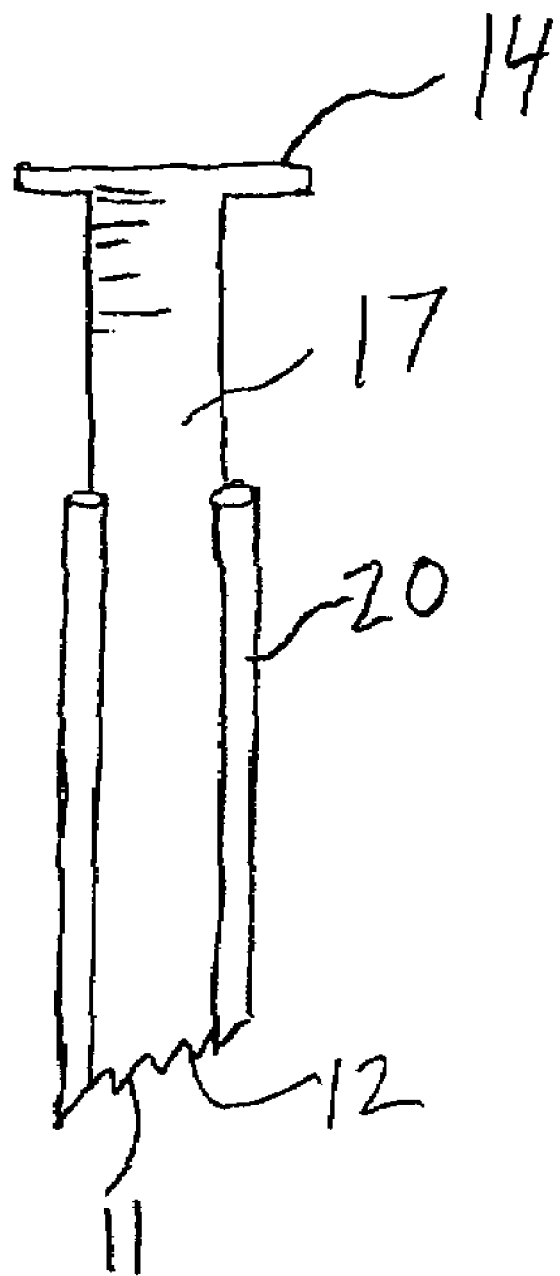
FIG. 2C is a front view of one preferred embodiment of a retractor of the invention.

As shown in FIGS. 2A-3, the retractor 1 is preferably provided with additional features that assist in properly placing the retractor 1 prior to anchoring the retractor 1 with a pin 60. FIG. 2C shows a retractor 1 having an angled leading end 12. The angle or slope of the leading end 12 is selected to generally match the natural slope of the bone along the periphery of the acetabular rim 102. The sloped leading end 12 assists in stabilizing the retractor 1 on the bone, in locating optimum placement of the retractor 1 along the rim 102, and in orienting the spacer portion 17 of the site anchor portion 10 in an advantageous position for retraction of the incision 110. Stability and positioning of the retractor 1 are further enhanced by providing the site anchor portion 10 with a curved or arcuate contour that generally matches the curve of the outer rim 102 of the acetabulum of the invention. Together, the angle/slope and arcuate contour provide a double contour functionality that is advantageous in MIS hip procedures.

FIGS. 2A-3 show a preferred embodiment of a retractor 1 having an extension portion 30 configured to engage a bony structure. As indicated in FIG. 3, the embodiment of FIG. 2 is particularly configured to rest along the outer portion of the rim 102 of the acetabulum 100. As indicated in the top view of FIG. 2B, the extension portion 30 has a curved dimension that generally matches the rim 102 of the acetabulum 100. The narrowed upright spacer portion 17 of the handle permits use of a mobile window at the plane of the skin without damaging the skin, which might occur with prior art broad retractors, while the broad leading end at the level of the bone provides wide visualization precisely where necessary.

As shown in FIG. 2A, a bone engagement structure 31, such as serrations, is preferably provided on the leading edge of the extension portion 30. A bone engagement structure 11 may also be provided on the leading edge 12 of the site anchor portion 10. In the embodiment of FIG. 2A, the bone engagement structure 11 is a series of serrations that include an angled edge 21 formed on a leading end 20L (see FIG. 1) of the retainer tracks 20. As shown in FIG. 2A, the leading edge 12 of the site anchor portion 10 preferably angles downward toward the extension portion 30, and the extension portion 30 in turn continues to angle downward, so as to form a generally continuous leading edge. The angled leading edge assists in placing the retainer 1 in a desired position along the acetabular rim 102.

As indicated in FIG. 3, in operation the site anchor portion is inserted into an incision 110. A leading end 12 of the site anchor portion 10 is placed at a selected location on the bone 100 of the patient, such as along an outer portion of the acetabular rim 102. The incision 110 is retracted using the retractor 1 in order to obtain a retracted position. A lengthwise pin 60 is inserted through the retainer track 20, and a leading portion 60L of the pin is secured in the bone of the patient. The pin 60 is then bent adjacent a trailing opening 20T of the retainer track 20 such that the pin 60 retains the retractor 1 in the retracted position. For further anchoring of the retractor 1, a second pin 60 can be inserted into a second retaining track 20 of the retractor 1, secured in the bone, and then bent.

Bending of the pin 60 can be achieved in various ways. In one preferred method, a driver is used to rotate the leading portion 60L of the pin 60 into bone 100, and the driver is then used to apply a bending force to the trailing end 60T of the pin 60 before removing the driver from the pin 60.

FIG. 4 shows two retractors 1 anchored with Steinmann pins 60 in an MIS hip procedure. As indicated in FIG. 4, the retractor of the invention can be used in conjunction with conventional retractors.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A retractor instrument assembly for use in a hip procedure in an acetabular area of a hip bone of a patient through an incision in the skin of the patient, comprising:
    a unibody retractor configured for anchorage to the hip bone via a bendable pin, said retractor comprising
        a site anchor portion, a leading end of said site anchor portion sized and configured to pass through a minimally invasive incision, a spacer portion of said site anchor portion extending upward from said leading end, said spacer portion having a narrow width to minimize tension in the skin along the incision,
        a surface support portion extending laterally from said spacer portion, a handle portion extending from said surface support portion, said handle portion configured for use in manipulating said retractor to retract the incision, at least one retainer track affixed to said spacer portion, said retainer track configured to closely receive a bendable pin therethrough for use in securing the retractor to the bone in a selected position, at least one bendable pin passing through said retainer track, a leading end of said bendable pin extending below said leading end of said site anchor portion, a bend formed in said pin above a trailing end of said retainer track, said bend preventing said retractor from sliding toward said trailing end of said bendable pin.

2. The assembly of claim 1, wherein said retainer track is a hollow tubular body having a continuous sidewall.

3. The assembly of claim 2, wherein said at least one retainer track is positioned along a side of said spacer portion.

4. The assembly of claim 3, further comprising a pair of retainer tracks, said retainer tracks positioned along opposing sides of said spacer portion.

5. The assembly of claim 4, further comprising an extension portion extending laterally along said leading end of said site anchor portion, said extension portion having a curved configuration for use in resting said extension portion substantially along an outer portion of a rim of the acetabulum.

6. The assembly of claim 5, wherein a leading end of said site anchor portion angles downward toward said extension portion, and said extension portion in turn continues to angle downward, so as to form a generally continuous angled leading edge for use in placing said retainer in a desired position along the acetabular rim of the patient.

7. The assembly of claim 6, wherein said generally continuous angled leading edge is serrated.

8. The assembly of claim 1, wherein said leading end of said site anchor portion is angled.

9. The assembly of claim 8, wherein said leading end of said site anchor portion is serrated.

10. The assembly of claim 9, wherein said site anchor portion has a curved configuration for use in resting said leading end of said site anchor portion substantially along an outer portion of a rim of the acetabulum.

11. The assembly of claim 1, wherein said leading end of said site anchor portion is serrated.

12. The assembly of claim 1, wherein said site anchor portion has a curved configuration for use in resting said leading end of said site anchor portion substantially along an outer portion of a rim of the acetabulum.

13. The assembly of claim 1, further comprising an extension portion extending laterally along said leading end of said site anchor portion, said extension portion having a curved configuration for use in resting said extension portion substantially along an outer portion of a rim of the acetabulum.

14. The assembly of claim 13, wherein said leading end of said site anchor portion angles downward toward said extension portion, and said extension portion in turn continues to angle downward, so as to form a generally continuous angled leading edge for use in placing said retainer in a desired position along the acetabular rim of the patient.

15. The assembly of claim 14, wherein said generally continuous angled leading edge is serrated.

16. A method of retracting an incision at a surgical site by anchoring a retractor on a bone of a patient comprising:

inserting a site anchor portion of a retractor into the incision, said retractor having at least one retainer track, seating a leading end of the site anchor portion at a selected location on the bone of the patient, retracting the incision using the retractor to thereby obtain a retracted position, inserting a lengthwise pin through said retainer track, securing a leading portion of said pin in the bone of the patient, bending said pin adjacent a trailing opening of said retainer track such that said pin retains said retractor substantially in said retracted position.

17. The method of claim 16, wherein said anchor portion has two retainer tracks.

18. The method of claim 17, further comprising inserting a second lengthwise pin through a second of said retainer tracks, securing a leading portion of said second pin in the bone of the patient, and bending said pin adjacent a trailing opening of said second retainer track such that said second pin assists in retaining said retractor substantially in said retracted position.

19. The method of claim 16, wherein the bone is a hip bone and the selected location is along a rim of an acetabulum of the hip bone.

* * * * *